United States Patent
Jubin, Jr. et al.

(10) Patent No.: US 6,914,167 B2
(45) Date of Patent: Jul. 5, 2005

(54) VENT RECOVERY SYSTEM

(75) Inventors: John C. Jubin, Jr., West Chester, PA (US); Te Chang, West Chester, PA (US)

(73) Assignee: Arco Chemical Technology, L.P., Greenville, DE (US)

(*) Notice: Subject to any disclaimer, the term of this patent is extended or adjusted under 35 U.S.C. 154(b) by 401 days.

(21) Appl. No.: 10/193,067

(22) Filed: Aug. 26, 2002

(65) Prior Publication Data

US 2004/0035754 A1 Feb. 26, 2004

(51) Int. Cl.$^7$ ................................................. C07C 7/10
(52) U.S. Cl. ........................................................ 585/867
(58) Field of Search ........................................... 585/867

(56) References Cited

U.S. PATENT DOCUMENTS

| 5,214,168 A | 5/1993 | Zajacek et al. ............. 549/531 |
| 5,468,885 A | 11/1995 | Jubin, Jr. ..................... 549/531 |

*Primary Examiner*—Thuan D Dang
(74) *Attorney, Agent, or Firm*—William C. Long

(57) ABSTRACT

A process for absorbing propylene from a gaseous propylene oxide process purge stream wherein propane liquid is used to absorb the propylene.

2 Claims, 2 Drawing Sheets

VENT RECOVERY SYSTEM

FIELD OF THE INVENTION

The present invention relates to an improved system for the treatment of purge gases from a process such as that for producing propylene oxide and to the separation and recovery of purge gas components.

DESCRIPTION OF THE PRIOR ART

In processes for the production of propylene oxide such as by reaction of hydrogen, oxygen and propylene over a palladium on titanium silicalite catalyst or by reaction of hydrogen peroxide with propylene (see, for example, U.S. Pat. No. 5,214,168), it is necessary to remove a purge or vent gas comprised of both oxygen and propylene. It is useful in such procedures to provide an inert diluent gas such as methane to prevent the formation of explosive oxygen/hydrocarbon mixtures; see U.S. Pat. No. 5,468,885.

In conventional systems, the gaseous purge stream is cooled to condense the condensable components and to reduce the size of the stream, and after separation of vapor from the liquid condensate, the vapor is fed to an absorber wherein it is contacted with a liquid absorbent which is effective to absorb $C_3$ hydrocarbons from the purge vapor. The absorber bottoms are stripped and the vapor is sent to a splitter where a bottoms propane purge is removed with the overhead propylene stream recycled to the process. As many as four distillation columns are normally employed.

U.S. Pat. No. 5,468,885 illustrates the use of isopropanol to absorb the $C_3$'s from the purge and suggests that other absorbents such as heptane, octane, methanol and acetone could be used.

SUMMARY OF THE INVENTION

In accordance with the present invention, propane is used to absorb propylene from the purge steam and this propane is largely vaporized into the vent from the absorber thus separating propane from the system.

DESCRIPTION OF THE DRAWINGS

The attached

Attached

DETAILED DESCRIPTION

Figure 1:
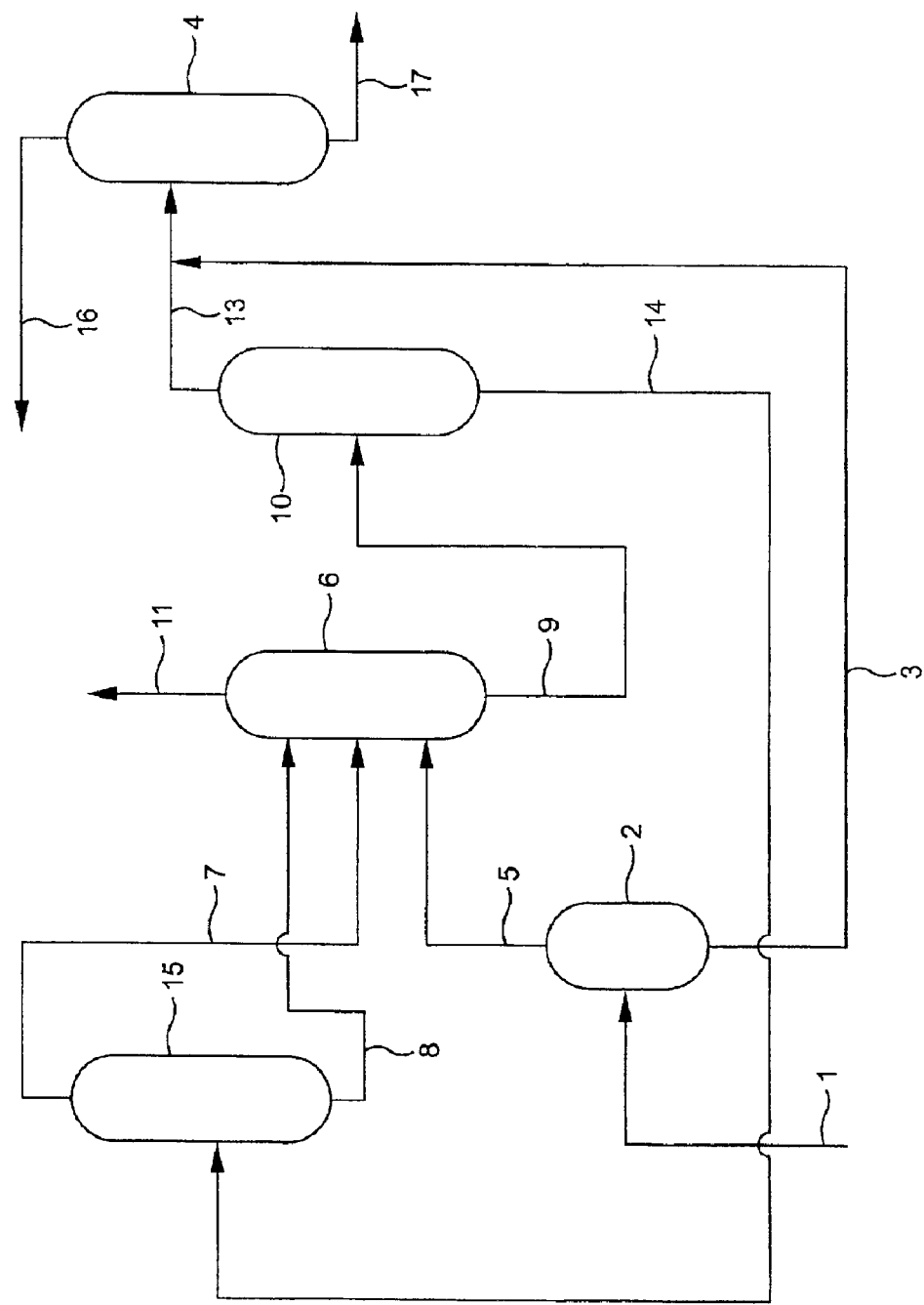
FIG. 1 illustrates in schematic form conventional practice for the treatment of propylene oxide process purge gas.

Referring to FIG. 1, in conventional practice, the gaseous propylene oxide purge stream, to which methane has been added, is cooled (not shown) and passed via line 1 to vapor-liquid separator 2. Liquid condensate, mainly $C_3$ hydrocarbons, passes from separator 2 via line 3 and then to splitter 4.

Uncondensed vapor passes from separator 2 via line 5 to absorber 6 wherein it is contacted in counter current flow with an absorbent liquid, illustratively a mixture of octane and hexane which are introduced to absorber 6 via lines 7 and 8 respectively. In absorber 6, absorption of the $C_3$ hydrocarbons takes place and a liquid stream comprised of the absorbent and absorbed materials passes via line 9 to stripper 10.

Vapors from absorber 6 are removed overhead via line 11 and are purged from the system. Generally, the hydrocarbons in this purge gas are used as fuel.

In stripper 10, $C_3$ hydrocarbons are stripped over head and pass via line 13 with condensate from separator 2 to splitter 4.

Bottoms from stripper 10 comprise the absorbent liquid and is passed to via line 14 to distillation column 15. In column 15 the absorbent liquid, illustratively hexane/octane, is separated by distillation with the heavier (octane) stream recovered as a bottoms stream which passes via line 8 to the upper part of absorber 6. The lighter absorbent (hexane) is recovered via line 7 and passes to absorber 6 where it is introduced at a point well below the point of introduction of the heavier component. In each case, the streams from column 15 are adjusted to an appropriate temperature (not shown) before being introduced into absorber 6.

Splitter 4 is a distillation column effective to separate propane and propylene. An overhead stream enriched in propylene is separated via line 16 and recycled to the propylene oxide process. The bottoms stream enriched in propane is separated via line 17 and used for fuel.

Figure 2:
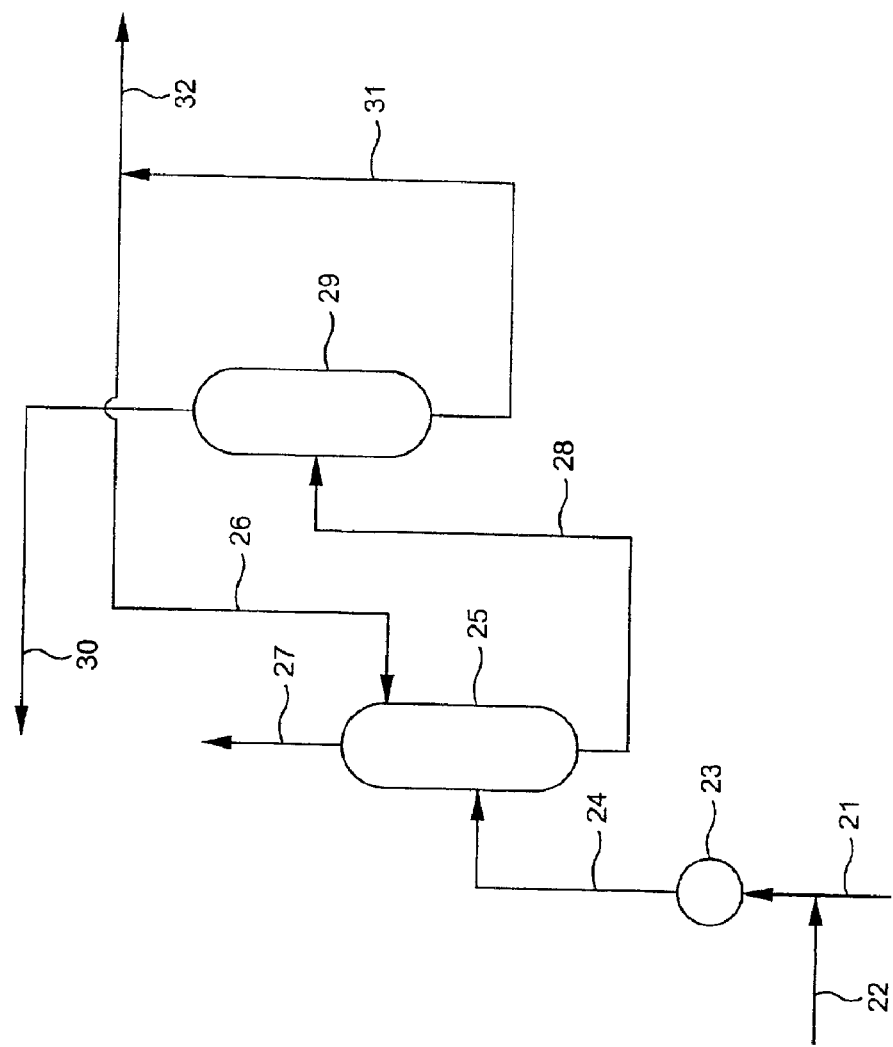
FIG. 2 illustrates in schematic form practice of the invention.

By way of contrast to the prior procedures, practice of the invention is illustrated in attached FIG. 2. Referring to FIG. 2, a purge gas stream from a propylene oxide process comprised of oxygen and $C_3$ hydrocarbons is fed to the system via line 21. Methane is added via line 22 in an amount sufficient to avoid the formation of explosive oxygen and hydrocarbon mixtures in the process. The combined stream is cooled in cooler 23 and the resulting vapor/liquid mixture is passed via line 24 to absorber 25. In the absorber, the cooled stream is contacted with a liquid recycle stream largely comprised of propane which is introduced into the upper portion of absorber 25 by means of line 26.

In absorber 25, the vapor passes upwardly with the contained propylene being absorbed into the propane absorbent. Vapors comprised of oxygen as well as inerts including methane, argon and the like as well as propane is removed from the upper portion of absorber 25 via line 27 and vented from the system. Suitably the vented gases containing substantial hydrocarbon are used as fuel.

The absorber bottoms stream passes via line 28 to splitter 29 wherein the mixture is separated into an overhead vapor stream concentrated in propylene which is removed by means of line 30 and recycled to the propylene oxide process. The bottoms from the splitter which is concentrated in propane is removed from splitter 29 by means of line 31 with a portion being discarded from the system via line 32 and used as fuel, and the remainder being recycled via line 26 to absorber 25. The amount of propane removed via line 32 is sufficient to balance the net propane which is introduced into the propylene oxide production system and/or is formed during the propylene oxide process.

Through practice of the above process, substantial economies of operation are achieved in that the number of distillation columns required to effect the recovery and recycle of propylene is reduced generally from four for conventional practice to just two for practice of the invention. In addition, the absorbent propane is indigenous to the reaction system since it comprises a usual substantial component of the propylene feed to the system and is usually made as a by-product. Thus, the absorptive separation in accordance with the invention does not require the introduction into the system of material which is not already found therein.

EXAMPLE

The following Example illustrates the invention. Referring to FIG. 2, a propylene oxide vent purge gas passes via line 21 at the rate of about 24867.9 lbs/hr and is combined with about 2727.3 lbs/hr methane which is introduced via line 22. The combined gas mixture comprises by weight about 7.9% oxygen, 0.3% hydrogen, 0.1% argon, 13.4% propylene, 66.9% propane, 0.1% water, 0.4% propylene oxide and 10.9% methane. This gas mixture is cooled to about 51° F. and at 1400 psi is fed to absorber 25 near the lower end. A liquid recycle propane stream at about 110° F. and 350 psi is fed to the upper end of absorber 25 via line 26 in amount of about 6000 lbs/hr and having a composition by weight of about 0.8% propylene, 98% propane and about 1.7% propylene oxide.

Absorber 25 is a conventional absorber wherein upwardly flowing vapor intimately contacts downflowing liquid. A vapor stream is removed via line 27 at about 50° F. and 400 psi and is used elsewhere as fuel. This vapor stream is removed at the rate of about 9778 lbs/hr and comprises by weight about 0.7% hydrogen, 0.2% argon, 22.0% oxygen, 0.8% propylene, 49% propane, 0.1% water, 0.1% propylene oxide and 27.3% methane.

A liquid bottoms stream at about 130° F. and 403 psi is removed at the rate of about 24818 lbs/hr from the absorber and is passed via line 28 to stripper 29. This stream comprises by weight about 0.2% oxygen, 14.8% propylene, 82.9% propane, 0.1% water, 0.6% propylene oxide and 1.4% methane.

Separation of propylene and propane takes place by distillation in stripper 29 with the overhead stream being removed via line 30 at the rate of about 11437 lbs/hr at 114° F. and 270 psi. This stream comprises by weight about 0.4% oxygen, 31.2% propylene, 65.2% propane, 0.2% water and 3% methane and is recycled to the propylene oxide production process.

Bottoms from the stripper is removed at the rate of about 13381 lbs/hr at 132° F. and 278 psi via line 31. This stream has a composition by weight of about 0.8% propylene, 98% propane, and 1.2% propylene oxide. The stream is divided with about 7381 lbs/hr being recovered via line 32 and used as fuel and about 6000 lbs/hr returning to absorber 25 via line 26 as above described.

From the above, it can be seen that propane is an effective absorbent to recover $C_3$ values in the propylene oxide process purge stream while the equipment necessary for the separation is markedly reduced as compared to conventional practices. In addition, utilities costs are significantly reduced.

We claim:

1. The process for recovering propylene contained together with propane and propylene oxide in a vapor purge from a propylene oxide process which comprises passing the said vapor purge to the lower section of an absorber, contacting said vapor purge with liquid propane absorbent introduced into the upper section of the absorber and absorbing propylene from said vapor purge in said liquid propane absorbent in a propylene absorption step, removing from the absorber a vapor stream comprised of propane and a liquid stream comprised of propylene and liquid propane absorbent, passing the liquid propane absorbent stream containing absorbed propylene to a distillation column, distilling overhead a stream comprised of propylene, recovering a bottoms stream comprised of propane, and recycling at least a portion of the said recovered propane stream to said propylene absorption.

2. The process of claim 1, wherein the vapor purge contains added methane in an amount sufficient to avoid explosive mixture formation.

* * * * *